United States Patent [19]

Herrmann

[11] Patent Number: 5,705,619
[45] Date of Patent: Jan. 6, 1998

[54] COMPLEXES OF LANTHANIDES WITH HETEROCYCLIC CARBENES

[75] Inventor: Wolfgang A. Herrmann, Freising, Germany

[73] Assignee: Hoechst Aktiengesellschaft, Germany

[21] Appl. No.: 581,398

[22] Filed: Dec. 29, 1995

[30] Foreign Application Priority Data

Dec. 29, 1994 [DE] Germany ............... 44 47 070.3

[51] Int. Cl.[6] .................................................. C07F 5/00
[52] U.S. Cl. ............................................. 534/10; 534/15
[58] Field of Search ............................... 534/10, 15

[56] References Cited

PUBLICATIONS

Shivhare et al., Chemical Abstracts, vol. 97, abstract 61895, 1982.
Panyushkin et al., Chemical Abstracts, vol. 100, abstract 202454, 1984.
Prabhakar et al., Chemical Abstracts, vol. 109, abstracts 179469, 1988.
Trikha et al., Chemical Abstracts, vol. 118, abstract 224264, 1993.
Vijayan et al., Chemical Abstracts, vol. 120, abstract 288451, 1994.
Evans et al., chemical Abstracts, vol. 121, abstract 72366, 1994.
Rabe et al., Chemical Abstracts, vol. 123, abstract 159312, 1995.
Evans et al., Chemical Abstracts, vol. 123, abstract 274319, 1995.
Angew. Chem. Int.Ed. Engl. 1994, 33 No. 17, Schumann et al.
Journal Am. Chem. Society, 1994, 116, 7927–7928, Arduengo et al.
Chemische Berichte, 1994, 127, 2369–2372 Schumann et al.

*Primary Examiner*—Richard L. Raymond
*Attorney, Agent, or Firm*—Bierman, Muserlian & Lucas

[57] ABSTRACT

A complex of the formula

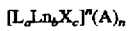

$$[L_aLn_bX_c]^r(A)_n$$

wherein Ln is an ion in the oxidation state of 2, 3 or 4 of the lanthanide elements having the atomic numbers 21, 39 and from 57 to 71 in the Periodic Table of the Elements, with the exception of europium and promethium, as central atom, $X^{(S)}$ are monodentate or multidentate, charged or uncharged ligands bound to the central atom and L is a monocarbene or dicarbene ligand likewise bound to the central atom and which are derived from imidazole and/or pyrazole, A is a singly charged anion or the chemical equivalent of a multiple charged anion, b is an integer from 1 to 4, a is an integer from 1 to 4 . b and c is zero or an integer from 1 to 4.b and n is zero or an integer from 1 to 3.b having catalytic activity.

10 Claims, No Drawings

COMPLEXES OF LANTHANIDES WITH HETEROCYCLIC CARBENES

The group of the rare earths comprises the 14 elements cerium, praseodymium, neodymium, promethium, samarium, europium, gadolinium, terbium, dysprosium, holmium, erbium, thulium, ytterbium, and lutetium ("rare earth metals"). Owing to their great chemical similarity, they are put together with the metals of the third transition group (Group 3 in accordance with the IUPAC recommendation 1985), namely scandium, yttrium and lanthanum, under the name lanthanide elements.

In their chemical compounds, the 17 elements of this group are predominantly trivalent, but individual representatives of the lanthanides form compounds in which they are tetravalent (e.g. cerium, terbium) and divalent (e.g. europium, ytterbium). The chemical compounds of the lanthanides are marked by predominantly ionic bonding and a pronounced tendency to bond to oxygen. The applications of the lanthanide compounds cover a wide variety and are derived, as a first approximation, from the Lewis acidity of the metal ions, particularly in the higher oxidation states, and from the electrochemical properties as reducing and oxidizing agents. Thus, tetravalenet cerium is a powerful single-electron oxidant. Divalent samarium is used in organic synthesis as a selecteive coupling reagent. Many lanthanides are suitable for doping incandescent lamp materials, because they greatly reduce the electron work function from metal alloys.

Almost all lanthanide ions are capable of solvation, i.e. of adding Lewis-base ligands (e.g. ethers, amines). These base additions frequently lead to improved solubility of the lanthanide compounds in organic solvents. At the same time, there is an increase in the hydrolytic stability, which is low in the case of simple lanthanide compounds such as halides. In addition, a frequently advantageous lowering of the Lewis acidity of the metal ions in question occurs.

If account is taken of the fact that numerous lanthanide compounds are active as catalysts in reactions of organic compounds, then the targeted control of the metal reactivity of the lanthanides is particularly desirable. In this context, importance attaches to sufficiently nucleophilic ligands which are stably, i.e. without formation of the usual dissociation equilibria, bound to the lanthanide ions. At the same time, they should be so widely variable in their make-up that they can be used in a targeted manner as stereo electronic control ligands for the reactivity of the lanthanides. Such control ligands have to be oxidation-resistant and should not react with other groups bound to the lanthanide ions. Furthermore, it is necessary for these ligands to increase the solubility in organic solvents of the lanthanide compounds to which they are bound. Finally, they must not experience any changes caused by the lanthanide ion beyond the complex formation.

Since most lanthanide ions are "hard cations" in the sense of the Pearson concept, (cf., for example, Römpp, Chemie-Lexikon, 1987, Vol. 5, page 3651 ff), these divalent, trivalent and tetravalent metal ions correspondingly prefer "hard bases", as ligands in the chemistry of the lanthanides. On the other hand, the electronically equivalent thioethers and phosphines are of only subsidiary importance, because as "soft Lewis bases", they are coordinately bonded significantly more weakly to the rare earth metal ions. In addition, they relatively easily undergo oxidation processes which lead to formation of sulfones, sulfur dioxides or phosphine oxides.

OBJECTS OF THE INVENTION

It is an object of the invention to provide complexes of the lanthanides which contain strongly coordinately bonded ligands and are resistant to oxidation processes.

This and other objects and advantages of the invention will become obvious from the following detailed description.

THE INVENTION

The novel Compounds of the invention have the formula

wherein Ln is an ion in the oxidation state 2, 3 or 4 of the lanthanide elements having the atomic numbers from 21, 39 and 57 to 71 in the Periodic Table of the Elements, with the exception of europium and promethium, as central atom, Xs are monodentate or mutidentate, charged or uncharged ligands bound to the central atom and L is selected from the group consisting of monocarbenes of the formulae

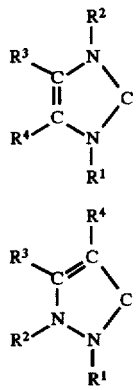

and dicarbenes of the formulae

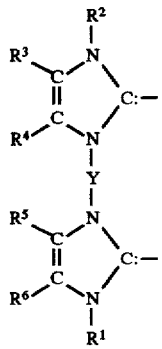

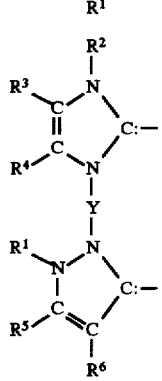

likewise bound to the central atom, wherein $R^1$, $R^2$, $R^3$, $R^4$, $R^5$ and $R^6$ are individually selected from the group consisting of sulfonated or unsulfonated alkyl of 1 to 7 carbon atoms, sulfonated or unsulfonated aliphatic monocyclics or polycyclics of 5 to 18 carbon atoms, sulfonated or unsulfonated alkenyl of 2 to 5 carbon atoms, sulfonated or unsulfonated aryl of 6 to 14 carbon atoms and sulfonated or unsulfonated arylalkyl of 7 to 19 carbon atoms or $R^3$, $R^4$, $R^5$ and $R^6$ can be hydrogen, or $R^3$ together with $R^4$ and $R^5$ together with $R^6$ can in each case also be individually fused and sulfonated or unsulfonated groups of 3 to 7 carbon atoms, Y is an optionally unsaturated alkylidene of 1 to 4 carbon atoms or dialkylsilylene or tetraalkyl-disilylene, A is a singly charged anion or the chemical equivalent of a multiply charged anion, b is an integer from 1 to 4, a is an integer from 1 to 4 . b and c is zero or an integer from 1 to 3 . b and n is zero or an integer from 1 to 3.b.

The literature to date makes only two references to complexes of the lanthanides of elements of atomic Nos. 57 to 71 with ligands which are derived from heterocyclic carbenes. The carbenes are here bound to the molecule fragments bis($\eta^5$-pentamethylcyclopentadienyl)-ytterbium or bis($\eta^5$-pentamethylcyclopentadienyl)-samarium. In the form of the pentadienyl radicals, these complexes contain strongly electron-donating $\pi$-ligands which are chemically and structurally not comparable with the conventional metal halides, alkoxides and amides (Arduengo et al., J. Am. Chem. Soc. 1994, Vol. 116, p. 7927 ff; Schumann et al., Angew. Chem., 1994, Vol. 106, p. 1829 ff).

In view of this prior art, it is surprising that carbenes derived fron nitrogen heterocycles can be coordinated as stably bound ligands to divalent, trivalent and tetravalent lanthanide ions without other additional organic ligands such as cyclopentadienyl or pentamethylcyclopentadienyl being present.

The new compounds are soluble in organic solvents, but also in water, particularly when they contain aliphatic or aromatic radicals substituted by sulfonates. They are thermally very stable and have a high oxidation stability.

The new compounds are derived from the elements scandium, yttrium, lanthanum, cerium, praseodymium, neodymium, samarium, gadolinium, terbium, dysprosium, holmium, eribum, thulium, ytterbium and lutetium in the oxidation states two, three and four. As a radioactive element, promethium is taken out of the group of lanthanides for the purposes of the present invention; europium is likewise excepted as an element very similar to the alkaline earth metal strontium and barium.

Monodentate or multidentate ligands which can be present in the complexes in addition to the carbenes and are denoted by X in formula I are hydrogen or hydrogen ion, halogens, or halides, pseudohalides, carboxylate ions, sulfonate ions, amides, alkoxides, acetylacetonates, carbon monoxide, nitrogen monoxide, nitriles, isonitriles, monoolefins or diolefins, alkynes and $\pi$-aromatics. If a plurality of these ligands are present in the complex molecule, they can be identical or different.

In the monocarbenes or dicarbenes derived from imidazole and from pyrazole or their derivatives and having the formulae II, III, IV and V, $R^1$ to $R^6$ are preferably methyl, isopropyl, tert-butyl, benzyl, tri-phenylmethyl, phenyl, tolyl, mesityl and adamantyl. $R^1$ and $R^2$ are preferably methyl, tert-butyl, phenyl, benzyl and o-tolyl. $R^3$ and $R^4$ are preferably hydrogen and methyl.

$R^3$ and $R^4$ and $R^5$ and $R^6$ can form a ring system together with two adjacent carbon atoms of the imidazole ring or the pyrazole ring. $R^3$ and $R^4$ or $R^5$ and $R^6$ are then preferably the moieties $(CH)_4$, which leads to formation of a fused aromatic six-membered ring, $(CH_2)_4$ and $(CH_2)_5$.

The bridges denoted by Y of the dicarbenes of formulae IV and V are preferably methylene, dimethylmethylene, diphenylmethylene, 1,3-phenylene and ethylidene. Among the silicon-containing bridges, dimethylsilylene and tetramethyldisilylene are preferred.

In formula I, b is preferably 1; A are preferably halide, pseudohalide, tetraphenylborate, tetrafluoroborate, hexafluorophosphate and carboxylate ions and more preferably acetate ion, also metal complex anions such as tetracarbonylcobaltate, hexafluoroferrarte (III), tetrachloroferrate, tetrachloroaluminate or tetrachloropalladate (II).

The compounds can be obtained by various routes. According to one method of preparation, free carbene which has been obtained from the associated azolium salt by deprotonation is reacted with a lanthanide compound. The carbene can previously have been isolated as such or is prepared in situ. Suitable lanthanide compounds are halides, carboxylates, acetylacetonates, trifluoromethanesulfonates, alkoxides, phenoxides, monoalkylamides and dialkylamides and monophenylamides and diphenylamides, alkoxides and alkylamides contain alkyls of 1 to 5 carbon atoms, these alkyls being able to be identical or different in the case of the dialkylamides.

A further route for preparing the new complexes is the direct reaction of a lanthanide compound with an azolium salt, i.e. without prior formation of a carbene from the azolium salt. The lanthanide compounds can be defined by the formula $LnZ_m$ (m=2, 3 or 4), where Z is a halide, pseudohalide, carboxylate, acetylacetonate, alkoxide of $C_1$–$C_5$-alkyls, phenoxide, monoalkylamide and dialkylamide of $C_1$–$C_5$-alkyls which can be identical or different in the case of the diamide, or disilylamide. The azolium salts correspond to the formula [L-H]Z or [L-H]A where L, Z and A are as defined above.

The reaction of the lanthanide compounds with the carbenes, and optionally, further ligands is carried out by mixing the reactants in a solvent at low temperatures (e.g. −78° C.), at room temperature or at an elevated temperature. The reaction proceeds rapidly and is often essentially complete after a few minutes. However, to complete the reaction, it is advisable to employ reaction times of up to a number of hours, particularly when the starting materials are only partially dissolved in the medium used, i.e. react from suspension.

To prepare water-soluble complexes containing sulfonated ligands, the starting materials include at least one reactant whose molecule or molecular fragment is sulfonated.

To isolate the new complexes from the reaction medium, it has been found to be useful to remove the solvent, advantageously in a high vacuum. The crude product is purified by washing and crystallization from a suitable solvent or solvent mixture which can be determiend in the individual case by preliminary experiments.

The lanthanide-carbene complexes of formlua I are catalysts for reactions which are catalyzed by Lewis acids, e.g. the preparation of polyactides (which are biodegradable polymers), and also for CH, CC, CSi and NC linkage reactions. These include the hydroamination, hydrogenation, oligomerization, polymerization of olefins, isomerization and hydrosilylation of olefins, hydroboration of olefins and alkynes, the Michael reaction, the Diels-Alder reaction, the Friedel-Crafts acylation of aromatics and the addition of Grignard reagents to 1,3-diketones.

In the following examples, there are described several preferred embodiments to illustrate the invention. However, it is to be understood that the invention is not intended to be limited to the specific embodiments.

EXAMPLE 1

Tris(1,3-dimethylimidazolin-2-ylidene)-erbium-trichloride (a) 22.6 ml of 0.14 molar solution of 1,3-dimethylimidazolin-2-ylidene in THF (corresponding to 3.25 mmol of carbene) were added dropwise to 0.508 g (1.0 mmol) of $ErCl_3(thf)_{3.25}$, suspended in 50 ml of tetrahydrofuran (THF;thf). The mixture was stirred for 3 days at room temperature and the solvent was then removed by filtration. After drying for 5 hours in a high vacuum at 0.1 Pa, 0.392 g (70%) of the analytically pure, yellow desired product were obtained.

(b) 1 mol-equivalent of $Er[N(SiMe_3)]_3$ (Me:—$CH_3$) and 3 mol-equivalents of 1,3-dimethylimidazolium chloride were suspended in 50 ml of THF and the suspension was refluxed for 5 days. After distilling off the solvent and drying for 6 hours in a high vacuum at 0.1 Pa, the analytically pure, yellow desired product was obtained.

Characterization $C_{15}H_{24}Cl_3ErN_6$; Molecular Weight=562.02 calc. % C 32.6 % H 4.3 % N 14.94 % Cl 18.92 found C 31.92 H 4.15 N 13.98 Cl 18.98

IR: v=3153 $cm^{-1}$ s, 3101 s, 1573 s, 1397 vs, 1313 s, 1221 vs, 1174 s, 1113 s, 1076 m, 1018 m, 1003 m, 972 m, 938 m, 917 m, 894 w, 740 vs, 648 w, 622 m, 609 w, 450 m.

MS (EI): m/2z=96 a.m.u. (100%) [carbene], 81 (4) [carbene-Me]

EXAMPLE 2

(1,3-dimethylimidazolin-2-ylidene)-(tetrahydrofuran)-tris[bis-(dimethylsilyl)-amido]-yttrium 4.2 ml of a 0.3 molar solution of 1,3-dimethylimidazolin-2-ylidene in THF (corresponding to 1.2 mmol of carbene) were slowly added dropwise to 0.756 g (1.2 mmol) of $Y(bdsa)_3(thf)_2$, amide (bdsa:bis(dimethylsilyl)amide) in 35 ml of THF. The mixture was stirred for 24 hours at room temperature and the solvent was distilled off. The product was extracted with 20 ml of n-hexane and after drying, 0.776 g (99%) of the greenish desired product were obtained in analytically pure quality.

Characterization $C_{21}H_{58}N_5OSi_6Y$; Molecular Weight=654.15 calc. % C 38.56 % H 8.94 % N 10.71 found C 38.37 H 8.61 N 10.56

IR: v=3169 $cm^{-1}$ w, 3135 w, 2070 vs, 1992 (sh)m, 1927 (sh)m, 1773 w, 1540 w, 1401 m, 1316 m, 1243 vs, 1220 m, 1169 w, 1154 w, 1112 m, 1048 (br)vs, 970 vs, 941 vs, 898 (br)vs, 836 vs, 788 vs, 763 vs, 724 s, 682 m, 624 w, 609 w, 446 w, 409 w.

1H-NMR ($C_6D_6$): δ=0.35 ppm (36 H, s, $SiCH_3$), 1.41 (4 H, d, THF), 3.38 (6 H, s, $NCH_3$), 3.56 (4 H, d, THF), 5.04 (6 H, SiH), 5.79 (2 H, s, CH).

$^{13}C\{^1H\}$-NMR: ($C_6D_6$): δ=3.2 ppm (q, $SiCH_3$), 25.7 (t, THF), 37.5 (q, NCH3), 67.9 (t, THF), 121.1 (d, CH), 168.2 (s, NCN).

EXAMPLE 3

Trans-bis (1,3-dimethylimidazolin-2-ylidene )tris[bis (dimethyl-silyl)amido]-yttrium 8.7 ml of a 0.3 molar solution of 1,3-dimethylimidazolin-2-ylidene in THF (corresponding to 2.4 mmol of carbene) were slowly added dropwise to 0.756 g (1.2 mmol) of $Y(bdsa)_3(thf)_2$, (bdsa: see Example 2), dissolved in 35 ml of THF. The mixture was stirred for 24 hours at room temperature and the solvent was distilled off. The product was extracted with 20 ml of n-hexane and after drying, 0.805 g (99%) of the pale brown desired product were obtained in analytically pure quality.

Characterization $C_{22}H_{58}N_7Si_6Y$; Molecular Weight=678.18 calc. % C 38.96 % H 8.62 % N 14.46 found C 38.78 H 8.70 N 14.50

IR: v=3163 $cm^{-1}$ w, 3130 w, 2088 m, 2040 (sh)m, 1532 w, 1400 m, 1312 w, 0.26 ppm (1247 s), 1240 s, 1216 m, 1169 w, 1155 w, 1104 w, 1032 s, 969 (sh)m, 936 s, 893 vs, 834 s, 781 s, 760 s, 728 s, 720 s, 693 w, 675 w, 615 w, 602 w, 445 w, 433 w.

1H-NMR ($C_6D_6$): δ=0.26 ppm (36 H, S, $SICH_3$), 3.70 (12 H, S, $NCH_3$), 5.10 (6 H, sep., SiH), 6.03 (4 H, s. CH).

$^{13}C\{^1H\}$-NMR ($C_6D_6$): δ=3.5 ppm ($SiCH_3$), 38.6 ($NCH_3$), 120.7 (CH), (NCN) not observed.

Various modifications of the complexes of the invention may be made without departing from the spirit or scope thereof and it is to be understood that the invention is intended to be limited only as defined in the appended claims.

What I claim is:

1. A complex of the formula

wherein Ln is an ion in the oxidation state 2, 3 or 4 of the lanthanide elements having the atomic numbers 21, 39 and from 57 to 71 in the Periodic Table of the Elements, with the exception of europium and promethium, as central atom, X are monodentate or multidentate, charged or uncharged ligands bound to the central atom and L is selected from the group consisting of monocarbenes of the formulae

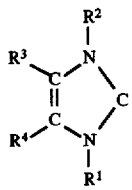

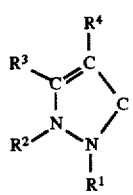

and dicarbenes of the formulae

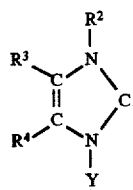

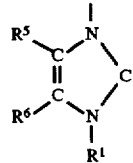

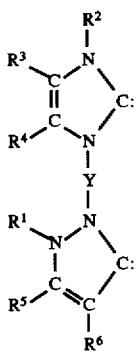

(V)

likewise bound to the central atom, wherein $R^1$, $R^2$, $R^3$, $R^4$, $R^5$ and $R^6$ are individually selected from the group consisting of sulfonated or unsulfonated alkyl of 1 to 7 carbon atoms, sulfonated or unsulfonated aliphatic monocyclics or poly-cyclics of 5 to 18 carbon atoms, sulfonated or unsulfonated alkenyl of 2 to 5 carbon atoms, sulfonated or unsulfonated aryl of 6 to 14 carbon atoms and sulfonated or unsulfonated arylalkyl of 7 to 19 carbon atoms or $R^3$, $R^4$, $R^5$ and $R^6$ can be hydrogen, or $R^3$ together with $R^4$ and $R^5$ together with $R^6$ can in each case also be individually fused and sulfonated or unsulfonated groups of 3 to 7 carbon atoms, Y is an optionally unsaturated alkylidene of 1 to 4 carbon atoms or dialkyl-silylene or tetraalkyt-disilylene, A is a singly charged anion or the chemical equivalent of a multiply charged anion, b is an integer from 1 to 4, a is an integer from 1 to 4.b and c is zero or an integer from 1 to 3.b and n is zero or 1 to 3.b.

2. A complex of claim 1 wherein X is selected from the group consisting of hydrogen, hydrogen ion, halogen, halogen ions, pseudohalides, carboxylate ions, sulfonate ions, amide, alkoxide, acetylacetonate, carbon monoxide, nitrogen monoxide, nitriles, isonitriles, monoolefins or diolefins, alkynes and π-aromatic.

3. A complex of claim 1 wherein $R^1$, $R^2$, $R^3$, $R^4$, $R^5$ and $R^6$ are individually selected from the group consisting of methyl, isopropyl, tert-butyl, benzyl, triphenylmethyl, phenyl, tolyl, xylyl, mesity and adamantyl.

4. A complex of claim 1 wherein $R^1$ and $R^2$ are individually selected from the group consisting of methyl, tert-butyl, phenyl, benzyl and o-tolyl.

5. A complex of claim 1 wherein $R^3$ and $R^4$ are hydrogen or methyl.

6. A complex of claim 1 wherein $R^3$ together with $R^4$ and $R^5$ together with $R^6$ are $(CH)_4$, $(CH_2)_4$, or $(CH_2)_5$.

7. A complex of claim 1 wherein Y is selected from the group consisting of methylene, dimethylmethylene, diphenylmethylene and ethylidene.

8. A complex of claim 1 wherein Y is dimethylsilyene or tetramethyldisilylene.

9. A complex of claim 1 wherein b is 1.

10. A complex of claim 1 wherein A is selected from the group consisting of a halide or pseudohalide ion, tetraphenylborate, tetrafluoroborate, hexafluorophosphate, acetate, tetracarbonylcobaltate, hexafluroferrate, tetrachloroferrate, tetrachloroaluminate and tetrachloropalladate ion.

* * * * *